United States Patent
Szmuszkovicz

[11] 3,966,736
[45] June 29, 1976

[54] 2,9-DIHYDRO-3H-PYRIDO[3,2-c]-s-TRIAZOLO[4,3-a][1,5]-BENZODIAZEPIN-3-ONES

[75] Inventor: Jacob Szmuszkovicz, Kalamazoo, Mich.

[73] Assignee: The Upjohn Company, Kalamazoo, Mich.

[22] Filed: Apr. 7, 1975

[21] Appl. No.: 565,709

[52] U.S. Cl. .......................... 260/268 PC; 424/250; 424/256; 260/295 A; 260/293.59; 424/267
[51] Int. Cl.² .................................... C07D 471/14
[58] Field of Search...... 260/295 A, 293.59, 268 PC

[56] References Cited
UNITED STATES PATENTS
3,850,942  11/1974  Hester et al. ............... 260/268 PC
3,903,105  9/1975  Gall ............................ 260/268 PC OTHER PUBLICATIONS
Hester, Jr.; Jackson B., Chemical Abstracts, vol. 7, 10,980v, (1970).
Hester, Jr.; Jackson B., Chemical Abstracts, vol. 75, 35974w, (1971).

*Primary Examiner*—Alton D. Rollins
*Assistant Examiner*—Jose Tovar
*Attorney, Agent, or Firm*—Hans L. Berneis

[57] ABSTRACT

2,9-Dihydro-3H-pyrido[3,2-c]-s-triazolo[4,3-a][1,5]-benzodiazepin-3-ones

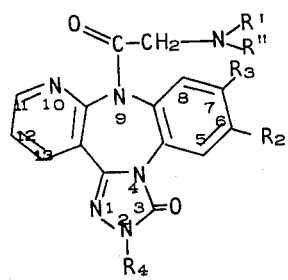

IV wherein R' and R'' are alkyl of 1 to 3 carbon atoms, inclusive; or the group

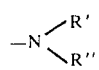

together is pyrrolidino, piperidino, 4-methylpiperazino or [4-(2-hydroxyethyl)]piperazino; wherein $R_2$ and $R_3$ are hydrogen, chloro, bromo, trifluoromethyl, or alkyl defined as above and wherein $R_4$ is hydrogen, alkyl as defined above or

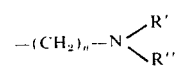

in which $n$ is the integer 2 or 3 or R', R'' or

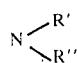

are defined as above, are obtained by reacting a compound of the formula I

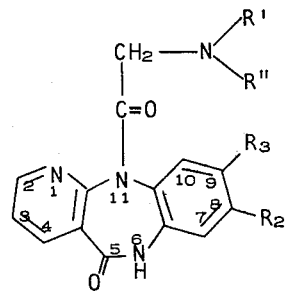

I wherein $R_2$, $R_3$, R', R'', or

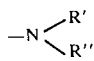

are defined as above, with phosphorus pentasulfide to give the corresponding 5-thione compound (II); treating II with an alkyl carbazate to obtain the compound of formula III:

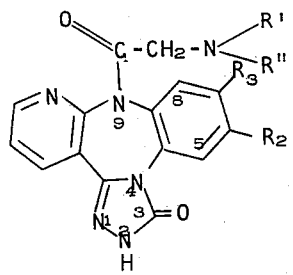

III wherein $R_2$, and $R_3$ are defined as above and treating III with an alkyl halide of 1 to 3 carbon atoms inclusive, or

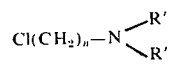

in which $n$, R', R'', or

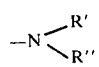

is defined as above, to obtain those compounds of formula IVA in which $R_4$ is alkyl or

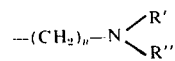

as defined above.

The compounds of formula IV (which include compounds III and IVA) and the pharmacologically acceptable acid addition salts thereof have sedative and anti-tussive activity and can be used in mammals.

10 Claims, No Drawings

2,9-DIHYDRO-3H-PYRIDO[3,2-c]-S-TRIAZOLO[4,3-a][1,5]-BENZODIAZEPIN-3-ONES

BACKGROUND OF THE INVENTION

FIELD OF THE INVENTION

This invention is directed to novel organic compounds and is particularly concerned with a 2,9-dihydro-3H-pyrido-[3,2-c]-s-triazolo[4,3-a][1,5]benzodiazepin-3-ones and a process of production therefor.

The new compounds and the process of production therefor can be illustratively represented as follows:

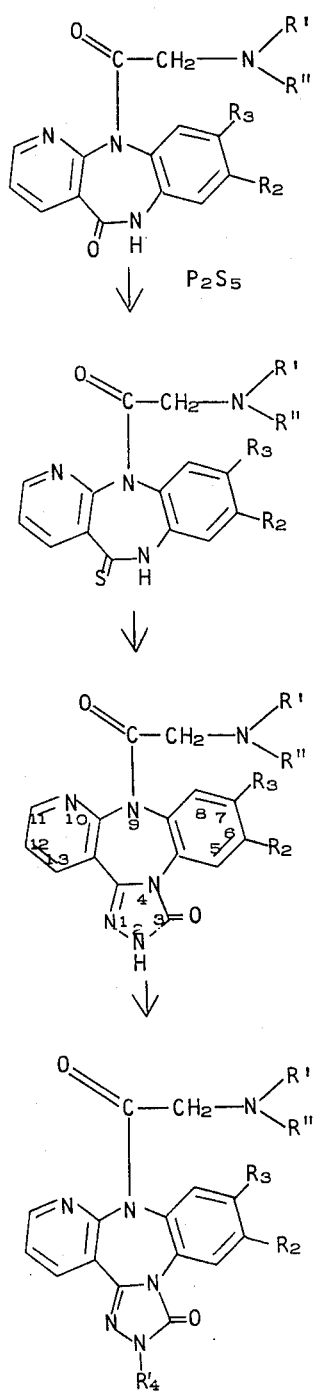

wherein R' and R'' are alkyl of 1 to 3 carbon atoms or the group

is pyrrolidino, piperidino, 4-methylpiperazino, or [4-(2-hydroxyethyl)]piperazino; wherein $R_2$ and $R_3$ are hydrogen, chloro, bromo, trifluoromethyl, or alkyl defined as above; and wherein $R'_4$ is alkyl as defined above or

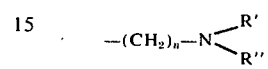

in which $n$ is the integer number 2 or 3 and R', R'', or

are defined as above.

The invention therefore has as objective compounds of the formula IV and the pharmacologically acceptable acid addition salts of the compounds of formula IV:

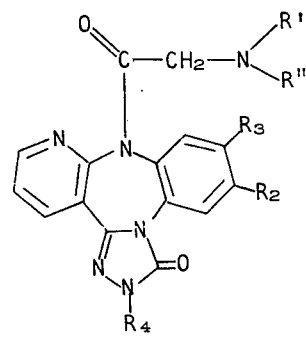

wherein $R_1$, $R_2$, and $R_3$ are defined as above and $R_4$ has the significance of hydrogen and $R'_4$ above.

The more desirable products of this invention are of the formula IVB:

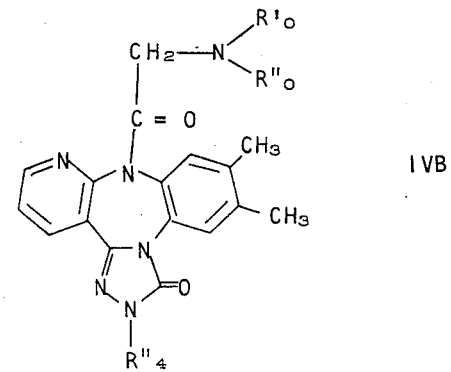

wherein $R'_o$, $R''_o$ are alkyl of 1 to 3 carbon atoms or together

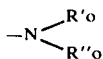

is 4-methylpiperazino or [4-(2-hydroxyethyl)-piperazino]; and wherein $R''_4$ is methyl or

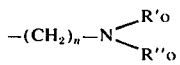

in which $n$ is the integer 2 or 3, and $R'_o$, $R''_o$, or

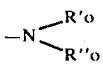

are defined as above, and the pharmacologically acceptable acid addition salts thereof.

The most desirable product of this invention are of the formula IVC:

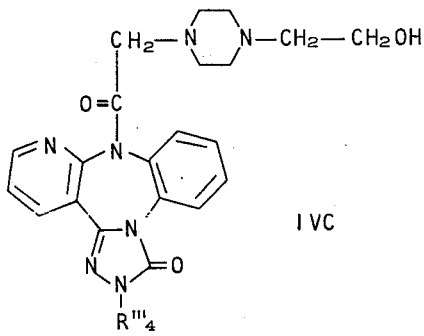

wherein $R'''_4$ is hydrogen or alkyl of 1 to 3 carbon atoms inclusive, and the pharmacologically acceptable acid addition salts thereof.

The process of this invention comprises: heating a compound of the formula I with phosphorus pentasulfide in an inert organic solvent to obtain the thione II; heating II with an alkyl carbazate to obtain the triazolone III and if desired treating III with an alkylating agent $R'_4X$ wherein X is chlorine, bromine or iodine and $R'_4$ is defined as above to obtain the corresponding compound of formula IV.

DESCRIPTION OF THE PREFERRED EMBODIMENT

Alkyl of 1 to 3 carbon atoms, inclusive, are exemplified by methyl, ethyl, propyl, and isopropyl.

The compounds of the formulae IV including acid addition salts thereof have sedative, tranquilizing, antitussive and muscle-relaxant effects in mammals, including man, and birds.

The acid addition salts of compounds of formula IV contemplated in this invention, are the hydrochlorides, hydrobromides, hydriodides, sulfates, phosphates, cyclohexanesulfamates, methanesulfonates and the like, prepared by reacting a compound of formula I with an excess of the selected pharmacologically acceptable acid.

Sedative effects of the novel compounds are shown by the following tests in mice:

Chimney test: [Med. Exp. 4, 145 (1961)]: The test determines the ability of mice to back up and out of a vertical glass cylinder within 30 seconds. At the effective dosage, 50% of the mice failed doing it.

Dish test: Mice in Petri dishes (10 cm. diameter, 5 cm. high, partially embedded in wood shavings) climb out in a very short time, when not treated. Mice remaining in the dish for more than 3 minutes indicates tranquilization. $ED_{50}$ equals the dose of the test compound at which 50% of the mice remain in the dish.

Pedestal test: The untreated mouse leaves the pedestal in less than a minute to climb back to the floor of the standard mouse box. Tranquilized mice will stay on the pedestal for more than 1 minute. At the $ED_{50}$ 50% of the mice have left the pedestal.

Nicotine antagonism test: Mice in a group of 6 are injected with the test compound. Thirty minutes later the mice including control (untreated) mice are injected with nicotine salicylate (2 mg./kg.). The control mice show overstimulation, i.e., (1) running convulsions followed by (2) tonic extensor fits followed by (3) death. an intraperitoneal dosage of the test compound protects 50% of the mice against (2) and (3).

The antitussive action is determined in rats by the method of Engelhorn et al., Arzneimittelforschung 13, 474 (1963) in which the number of coughs per 30 minutes of treated and untreated rats is measured. For reason of comparison codeine-treated rats are often added to the experiment.

In these experiments the novel compounds showed their efficacy as well as low toxicity (measurements of $LD_{50}$) at a level of 2–30 mg/kg. preferably 5–20 mg./kg. In larger animals, more than 10 kg., the low unit dosages are preferably such as 1–10 mg. for each kg.

The pharmaceutical forms contemplated by this invention include pharmaceutical compositions suited for oral, parenteral, and rectal use, e.g. tablets, powder packets, cachets, dragees, capsules, solutions, suspensions, sterile injectable forms, suppositories, bougies and the like. Suitable diluents or carriers such as carbohydrates (lactose), proteins, lipids, calcium phosphate, cornstarch, stearic acid, methylcellulose and the like may be used as carriers or for coating purposes. Water and oils, e.g., coconut oil, sesame oil, safflower oil, cottonseed oil, or peanut oil may be used for preparing solutions or suspensions of the active drugs. Sweetening, coloring, and flavoring agents may be added.

For mammals and birds, food premixes, with starch, oatmeal, dried fishmeat, fishmeal, flour and the like can be prepared.

The starting compounds of formula I are partially known in the art (German Auslegesahrift No. 1,620,523) or can be obtained as shown in the preparations.

In carrying out the process a selected 11-aminoacetyl-11H-pyrido[2,3-b][1,5]benzodiazepine-5-(6H)-one I is treated with phosphorus pentasulfide in an inert organic solvent. In the preferred embodiment of the invention, the reagent, $P_2S_5$, may be used in a slight molar excess of 5–10% of the stoichiometrically calculated amount. As solvent pyridine dioxane, picoline, benzene or the like may be used, and the reaction mixture is heated to between 50° C. and the reflux temperature of the mixture. The reaction period is between 1 to 12 hours. At the termination of the reaction the solvent is removed (by vacuum distillation preferably) and the residue is recovered by extraction e.g. with chloroform, ethyl acetate, benzene, or the like. Evaporation of the solvent used in the extraction, gives the product II which can be purified by conventional means e.g. additional extractions, crystallization, or chromatography.

Compound II is heated with an alkyl carbazate of the formula:

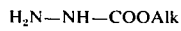

In which the alkyl group is of 1 to 3 carbon atoms, inclusive. Usually ethyl carbazate is preferred, but higher alkyl carbazates are operative. In the preferred embodiment of this invention, compound II is heated with ethyl carbazate in large excess for 1/10 hour to 3 hours at 190° to 250° C. in an oil bath. The alkyl carbazate serves simultaneously as reagent and solvent. The product usually precipitates upon cooling of the reaction mixture and is recovered by filtration and purified by conventional means, e.g., extractions of impurities, chromatography or most commonly by recrystallization. The triazolone compound III is thus obtained.

Alkylation of III is achieved by reacting the product III with a strong base e.g. sodium or potassium hydride in an organic solvent, e.g. dimethylformamide, diethylformamide, diethylacetamide, tetrahydrofuran, dioxane, benzene or the like with an excess of the base, followed by reacting the alkali metal salt thus formed with $R'_4X$ in which X is chlorine, bromine, or iodine and $R'_4$ is defined as herein before. Both reactions, formation of salt and the reaction of this salt with $R'_4X$ are usually performed at elevated temperatures between 50° to 125° C. The conversion of III to its alkali salt is usually performed during 15–25 minutes. The reaction of the salt with the halide is carried out during a longer period of time by keeping the reaction mixture at the elevated temperature for 1 to 36 hours. The product IVA thus obtained is isolated and purified by conventional means e.g. extraction, crystallization, chromatography, and the like.

The following preparations and examples are illustrative of the processes and products of the present invention, but are not to be construed as limiting.

PREPARATION 1

6,11-Dihydro-8,9-dibromo-5H-pyrido-[2,3-b][1,5]benzodiazepin-5-one

A mixture of 0.1 mole of 2-bromonicotinic acid and 0.1 mole of 1,2-diamino-4,5-dibromobenzene is heated in an open vessel to 150° C. with vigorous stirring. After 3 minutes the source of heat is removed, and the reaction mixture is allowed to cool to room temperature and to crystallizes to give a solid. The solid is removed from the vessel, powdered, washed with dilute sodium hydroxide, and then with boiling water, and finally recrystallized from dioxane to give 6,11-dihydro-8,9-dibromo-5H-pyrido[2,3-b][1,5]benzodiazepin-5-one.

If in this preparation 1,2-diamo-4,5-dibromobenzene is replaced with 1,2-diamio-4-bromobenzene, mixtures of 6,11-dihydro-8-(and 9-)bromo-5H-pyrido[2,3-b][1,5]benzodiazepine-5-ones are obtained. Isomeric mixtures are obtained in general in this reaction if only one substituent is present in the reagent 1,2-diaminobenzene.

PREPARATION 2

8,9-Dibromo-6,11-dihydro-11-[[4-(2-hydroxyethyl)-piperazino]acetyl]-5H-pyrido[2,3-b][1,5]benzodiazepin-5-one a.)
11-Chloroacetyl-8,9-dibromo-6,11-dihydro-5H-pyrido[2,3-b][1,5]benzodiazepin-5-one.

6,11-Dihydro-8,9-dibromo-5H-pyrido[2,3-b][1,5]benzodiazepin-5-one (0.1 mol) in 300 ml. of water-free dioxane is dissolved by heating to reflux. To the boiling solution is added, dropwise over 30 minutes, a solution of 15. g. (0.14 mol) of chloroacetyl chloride, dissolved in 40 ml. of water-free dioxane, and simultaneously 14.4 (0.14 mol) of triethylamine, dissolved in 30 ml. of water-free dioxane. The mixture is refluxed for 8 hours and then filtered while hot. The filtrate is evaporated in vacuo, and the resulting residue is recrystallized from acetonitrile to give 11-chloroacetyl-8,9-dibromo-6,11-dihydro-5H-pyrido[2,3-b][1,5]benzodiazepin-5-one.

b.)
8,9-Dibromo-6,11-dihydro-11[[4-(2-hydroxyethyl)-piperazino]acetyl]-5H-pyrido[2,3-b][1,5]benzodiazepin-5-one.

11-Chloroacetyl-8,9-dibromo-6,11-dihydro-5H-pyrido[2,3-b][1,5]benzodiazepin-5-one (0.05 mole) and 0.13 mole 4-(2-hydroxyethyl)piperazine, dissolved in 800 ml. ethanol are heated to reflux for a period of 20 hours. The hot solution is then filtered, the filtrate evaporated in vacuo and the remaining residue recrystallized from 2-propanol to give 8,9-dibromo-6,11-dihydro-11-[[4-(2- hydroxyethyl)piperazino]acetyl]-5H-pyrido[2,3-b][1,5]-benzodiazepin-5-one.

In the manner given in the preparations 1, 2a and 2b, other starting compounds of formula I are produced. Representative compounds thus produced include:

8,9-dibromo-6,11-dihydro-11-[(diethylamino)acetyl]-5H-pyrido[2,3-b][1,5]benzodiazepin-5-one;
8,9-dibromo-6,11-dihydro-11-[(dimethylamino)acetyl]-5H-pyrido[2,3-b][1,5]benzodiazepin-5-one;
8,9-dibromo-6,11-dihydro-11-[(dipropylamino)acetyl]-5H-pyrido[2,3-b][1,5]benzodiazepin-5-one;
8,9-dimethyl-6,11-dihydro-11-[(dipropylamino)acetyl]-5H-pyrido[2,3-b][1,5]benzodiazepin-5-one;
8,9-dimethyl-6,11-dihydro-11-[(dimethylamino)acetyl]-5H-pyrido[2,3-b][1,5]benzodiazepin-5-one;
8,9-dichloro-6,11-dihydro-11-[(diethylamino)acetyl]-5H-pyrido[2,3-b][1,5]benzodiazepin-5-one;
8,9-dichloro-6,11-dihydro-11-[(dimethylamino)acetyl]-5H-pyrido[2,3-b][1,5]benzodiazepin-5-one;

8- and 9-chloro-6,11-dihydro-11-[(dimethylamino)acetyl]-5H-pyrido[2,3-b][1,5]benzodiazepin-5-one;

8- and 9-fluoro-6,11-dihydro-11-[(dipropylamino)acetyl]-5H-pyrido[2,3-b][1,5]benzodiazepin-5-one;

8,9-difluoro-6,11-dihydro-11-[(dipropylamino)acetyl]-5H-pyrido[2,3-b][1,5]benzodiazepin-5-one;

8,9-di(trifluoromethyl)-6,11-dihydro-11-[(dipropylamino)-acetyl]-5H-pyrido[2,3-b][1,5]benzodiazepin-5-one;

8,9-dimethyl-6,11-dihydro-11-[[4-(2-hydroxyethyl)piperazino]-acetyl]-5H-pyrido[2,3-b][1,5]benzodiazepin-5-one;

8,9-dimethyl-6,11-dihydro-11-(pyrrolidinoacetyl)-5H-pyrido[2,3-b][1,5]benzodiazepin-5-one;

8,9-diethyl-6,11-dihydro-11-(pyrrolidinoacetyl)-5H-pyrido[2,3-b][1,5]benzodiazepin-5-one;

8,9-diethyl-6,11-dihydro-11-(piperidinoacetyl)-5H-pyrido-[2,3-b][1,5]benzodiazepin-5-one;

8,9-diisopropyl-6,11-dihydro-11-(piperidinoacetyl)-5H-pyrido[2,3-b][1,5]benzodiazepin-5-one;

8,9-diisopropyl-6,11-dihydro-11-[(4'-methylpiperazino)-acetyl]-5H-pyrido[2,3-b][1,5]benzodiazepin-5-one;

8,9-dimethyl-6,11-dihydro-11-[(4-methylpiperazino)acetyl]-5H-pyrido[2,3-b][1,5]benzodiazepin-5-one;

8-chloro-9-fluoro- and 9-chloro-8-fluoro-6,11-dihydro-11-[[4-(2-hydroxyethyl)piperazino]acetyl]-5H-pyrido[2,3-b]-[1,5]benzodiazepin-5-one;

6,11-dihydro-11-[[-(2-hydroxyethyl)piperazino]acetyl]-5H-pyrido[2,3-b][1,5]benzodiazepin-5-one;

6,11-dihydro-11-[(dimethylamino)acetyl]-5H-pyrido[2,3-b]-[1,5]benzodiazepin-5-one;

6,11-dihydro-11-(piperidinoacetyl)-5H-pyrido[2,3-b][1,5]-benzodiazepin-5-one;

6,11-dihydro-11-[(dipropylamino)acetyl]-5H-pyrido[2,3-b][1,5]benzodiazepin-5-one;

6,11-dihydro-11-(pyrrolidinoacetyl)-5H-pyrido[2,3-b]-[1,5]benzodiazepin-5-one;

6,11-dihydro-11-[(diethylamino)acetyl]-5H-pyrido[2,3-b][1,5]benzodiazepin-5-one;

and the like.

EXAMPLE 1

6,11-Dihydro-11-[(dimethylamino)acetyl]-5H-pyrido[2,3-b][1,5]benzodiazepin-5-thione A mixture of 6,11-dihydro-11-[(dimethylamino)acetyl]-5H-pyrido[2,3-b][1,5]benzodiazepin-5-one (0.14 mole), phosphorus pentasulfide (0.155 mole) and 1200 ml. of pyridine is heated at reflux temperature for 24 hours and the pyridine is then evaporated. Methylene chloride and water are added, and the organic layer is separated (some solid is present), washed with aqueous sodium bicarbonate until only a trace of solid is present, then with saturated salt solution, dried over anhydrous magnesium sulfate and evaporated. Trituration of the residue with methanol gives a solid which after crystallization from methylene chloride-methanol gives the product 6,11-dihydro-11-[(dimethylamino)acetyl]-5H-pyrido[2,3-b][1,5]benzodiazepin-5-thione.

EXAMPLE 2

6,11-Dihydro-11-[(dipropylamino)acetyl]-5H-pyrido[2,3-b][1,5]benzodiazepin-5-thione In the manner given in Example 1, 6,11-dihydro-11-[(dipropylamino)acetyl]-5H-pyrido[2,3-b][1,5]benzodiazepin-5-one is reacted with phosphorus pentasulfide in pyridine to give 6,11-dihydro-11-[(dipropylamino)acetyl]-5H-pyrido[2,3-b][1,5]benzodiazepin-5-thione.

EXAMPLE 3

8,9-Dimethyl-6,11-dihydro-11-[(dipropylamino)-acetyl]-5H-pyrido[2,3-b][1,5]benzodiazepin-5-thione In the manner given in Example 1, 8,9-dimethyl-6,11-dihydro-11-[(dipropylamino)acetyl]-5H-pyrido[2,3-b][1,5]benzodiazepin-5-one is reacted with phosphorus pentasulfide in pyridine to give 8,9-dimethyl-6,11-dihydro-11-[(dipropylamino)acetyl]-5H-pyrido[2,3-b][1,5]benzodiazepin-5-thione.

EXAMPLE 4

8,9-Dichloro-6,11-dihydro-11-[(dipropylamino)-acetyl]-5H-pyrido[2,3-b][1,5]benzodiazepin-5-thione In the manner given in Example 1, 8,9-dichloro-6,11-dihydro-11-[(dipropylamino)acetyl]-5H-pyrido[2,3-b][1,5]-benzodiazepin-5-one is reacted with phosphorus pentasulfide in pyridine to give 8,9-dichloro-6,11-dihydro-11-[(dipropylamino)acetyl]-5H-pyrido[2,3-b][1,5]benzodiazepin-5-thione.

EXAMPLE 5

8,9-Dibromo-6,11-dihydro-11-[(diethylamino)-acetyl]-5H-pyrido[2,3-b][1,5]benzodiazepin-5-thione In the manner given in Example 1, 8,9-dibromo-6,11-dihydro-11-[(diethylamino)acetyl]-5H-pyrido[2,3-b][1,5]-benzodiazepin-5-one is reacted with phosphorus pentasulfide in pyridine to give 8,9-dibromo-6,11-dihydro-11-[(diethylamino)acetyl]-5H-pyrido[2,3-b][1,5]benzodiazepin-5-thione.

EXAMPLE 6

6,11-Dihydro-11-[[4-(2-hydroxyethyl)piperazino]-acetyl]-5H-pyrido[2,3-b][1,5]benzodiazepin-5-thione In the manner given in Example 1, 6,11-dihydro-11-[[4-(2-hydroxymethyl)piperazino]acetyl]-5H-pyrido[2,3-b][1,5]-benzodiazepin-5-one is reacted with phosphorus pentasulfide in pyridine to give 6,11-dihydro-11-[[4-(2-hydroxyethyl)piperazino]acetyl]-5H-pyrido[2,3-b][1,5-benzodiazepin-5-thione.

EXAMPLE 7

8,9-Dibromo-6,11-dihydro-11-[[4-(2-hydroxyethyl)piperazino]acetyl]-5H-pyrido[2,3-b][1,5]benzodiazepin-5-thione In the manner given in Example 1, 8,9-dibromo-6,11-dihydro-11-[[4-(2-hydroxyethyl)piperazino]acetyl]-5H-pyrido[2,3-b][1,5]benzodiazepin-5-one is reacted with phosphorus pentasulfide in pyridine to give 8,9-dibromo-6,11-dihydro-11-[[4-(2-hydroxyethyl)piperazino]acetyl]-5H-pyrido[2,3-b][1,5]benzodiazepin-5-thione.

EXAMPLE 8

6,11-Dihydro-11-(pyrrolidinoacetyl)-5H-pyrido-[2,3-b][1,5]benzodiazepin-5-thione In the manner given in Example 1, 6,11-dihydro-11-(pyrrolidinoacetyl)-5H-pyrido[2,3-b][1,5]benzodiazepin-5-one is reacted with phosphorus pentasulfide in pyridine to give 6,11-dihydro-11-(pyrrolidinoacetyl)-5H-pyrido-[2,3-b][1,5]benzodiazepin-5-thione.

EXAMPLE 9

6,11-Dihydro-11-(piperidinoacetyl)-5H-pyrido-[2,3-b][1,5]benzodiazepin-5-thione

In the manner given in Example 1, 6,11-dihydro-11-(piperidinoacetyl)-5H-pyrido[2,3-b][1,5]benzodiazepin-5-one is reacted with phosphorus pentasulfide in pyridine to give 6,11-dihydro-11-(piperidinoacetyl)-5H-pyrido-[2,3-b][1,5]benzodiazepin-5-thione.

EXAMPLE 10

6,11-Dihydro-11-[(4-methylpiperazino)acetyl]-5H-pyrido[2,3-b][1,5]benzodiazepin-5-thione In the manner given in Example 1, 6,11-dihydro-11-[(4-methylpiperazino)acetyl]-5H-pyrido[2,3-b][1,5]benzodiazepin-5-one is reacted with phosphorus pentasulfide in pyridine to give 6,11-dihydro-11-[(4-methylpiperazino)-acetyl]-5H-pyrido[2,3-b][1,5]benzodiazepin-5-thione.

EXAMPLE 11

8,9-Dimethyl-6,11-dihydro-11-[(4-methylpiperazino)acetyl]-5H-pyrido[2,3-b][1,5]benzodiazepin-5-thione In the manner given in Example 1, 8,9-dimethyl-6,11-dihydro-11-[(4-methylpiperazino)acetyl]-5H-pyrido[2,3-b][1,5]benzodiazepin-5-one is reacted with phosphorus pentasulfide in pyridine to give 8,9-dimethyl-6,11-dihydro-11-[(4-methylpiperazino)acetyl]-5H-pyrido[2,3-b][1,5]benzodiazepin-5-thione.

EXAMPLE 12

8,9-Dimethyl-6,11-dihydro-11-[[4-(2-hydroxyethyl)-piperazino]acetyl]-5H-pyrido[2,3-b][1,5]benzodiazepin-5-thione In the manner given in Example 1, 8,9-dimethyl-6,11-dihydro-11-[[4-(2-hydroxyethyl)-piperazino]acetyl]-5H-pyrido[2,3-b][1,5]benzodiazepin-5-one is reacted with phosphorus pentasulfide in pyridine to give 8,9-dimethyl-6,11-dihydro-11-[[4-(2-hydroxyethyl)piperazino]acetyl]-5H-pyrido[2,3-b][1,5]benzodiazepin-5-thione.

In the manner given in the preceding examples other compounds corresponding to formula II can be synthesized. Representative compounds, thus obtained, include:

8,9-difluoro-6,11-dihydro-11-[(dipropylamino)acetyl]-5H-pyrido[2,3-b][1,5]benzodiazepin-5-thione;
8,9-di(trifluoromethyl)-6,11-dihydro-11-[(dipropylamino)-acetyl]-5H-pyrido[2,3-b][1,5]benzodiazepin-5-thione;
8,9-di(trifluoromethyl)-6,11-dihydro-11-[(diethylamino)-acetyl]-5H-pyrido[2,3-b][1,5]benzodiazepin-5-thione;
8-chloro-9-fluoro- and 9-chloro-8-fluoro-6,11-dihydro-11-[[4-(2-hydroxyethyl)piperazino]acetyl]-5H-pyrido[2,3-b]-[1,5]benzodiazepin-5-thione;
8,9-dimethyl-6,11-dihydro-11-[(dimethylamino)acetyl]-5H-pyrido[2,3-b][1,5]benzodiazepin-5-thione;
8,9-difluoro-6,11-dihydro-11-[(dipropylamino)acetyl]-5H-pyrido[2,3-b][1,5]benzodiazepin-5-thione;
8,9-diethyl-6,11-dihydro-11-(pyrrolidinoacetyl)-5H-pyrido[2,3-b][1,5]benzodiazepin-5-thione;
8,9-diisopropyl-6,11-dihydro-11-(piperidinoacetyl)-5H-pyrido[2,3-b][1,5]benzodiazepin-5-thione;

and the like.

EXAMPLE 13

2,9-Dihydro-9-[(dimethylamino)acetyl]-3H-pyrido[3,2-c]-s-triazolo[4,3-a][1,5]benzodiazepin-3-one A mixture of 6,11-dihydro-11-[(dimethylamino)acetyl]-5H-pyrido[2,3-b][1,5]benzodiazepin-5-thione (0.12 mole) and ethyl carbazate (1.2 mole) is heated in an oil bath preheated to 195°–205° C. using a take-off condenser (45 ml. is removed). The resulting solid is mixed with methylene chloride-water and the suspension is filtered. The filtrate is separated into layers, and the organic layer is washed with water, then brine solution and dried over anhydrous magnesium sulfate. The solvent is then evaporated and the resulting residue is repeatedly crystallized from methylene chloride to give 2,9-dihydro-9-[(dimethylamino)acetyl]-3H-pyrido[3,2-c]-s-triazolo[4,3-a][1,5]-benzodiazepin-3-one.

EXAMPLE 14

2,9-Dihydro-9-[(dipropylamino)acetyl]-3H-pyrido[3,2-c]-s-triazolo[4,3-a][1,5]benzodiazepin-3-one In the manner given in Example 13, 6,11-dihydro-11-[(dipropylamino)acetyl]5H-pyrido[2,3-b][1,5]benzodiazepin-5-thione is heated to about 200° C. with ethyl carbazate to give 2,9-dihydro-9-[(dipropylamino)acetyl]-3H-pyrido-[3,2-c]-s-triazolo[4,3-a][1,5]benzodiazepin-3-one.

EXAMPLE 15

6,7-Dimethyl-2,9-dihydro-9-[(dipropylamino)-acetyl]-3H-pyrido[3,2-c-]-s-triazolo[4,3-a][1,5]benzodiazepin-3-one In the manner given in Example 13, 8,9-dimethyl-6,11-dihydro-11-[(dipropylamino)acetyl]-5H-pyrido[2,3-b][1,5]-benzodiazepin-5-thione is heated to about 200° C. wth ethyl carbazate to give 6,7-dimethyl-2,9-dihydro-9-[(dipropylamino)-acetyl]-3H-pyrido[3,2-c]-s-triazolo[4,3-a][1,5]benzodiazepin-3-one.

EXAMPLE 16

6,7-Dichloro-2,9-dihydro-9-[(dipropylamino)-acetyl]-3H-pyrido[3,2-c]-s-triazolo[4,3-a][1,5]benzodiazepin-3-one In the manner given in Example 13, 8,9-dichloro-6,11-dihydro-11-[(dipropylamino)acetyl]-5H-pyrido[2,3-b][1,5]-benzodiazepin-5-thione is heated to about 200° C. with ethyl carbazate to give 6,7- dichloro-2,9-dihydro-9-[(dipropylamino)acetyl]-3H-pyrido[3,2-c]-s-triazolo-[4,3-a][1,5]benzodiazepin-3-one.

EXAMPLE 17

6,7-Dibromo-2,9-dihydro-9-[(diethylamino)-acetyl]-3H-pyrid[3,2-c]-s-triazolo[4,3-a][1,5]benzodiazepin-3-one In the manner given in Example 13, 8,9-dibromo-6,11-dihydro-11-[(diethylamino)acetyl]-5H-pyrido[2,3 -b][1,5]-benzodiazepin-5-thione is heated to about 200° C. with ethyl carbazate to give 6,7-dibromo-2,9-dihydro-9-[(diethylamino)-acetyl]-3H-pyrido[3,2-c]-s-triazolo[4,3-a][1,5]benzodiazepin-3-one.

EXAMPLE 18

2,9-Dihydro-9-[[4-(2-hydroxyethyl)piperazino]-acetyl]-3H-pyrido[3,2-c]-s-triazolo[4,3-a][1,5]benzodiazepin-3-one In the manner given in Example 13, 6,11-dihydro-11-[[4-(2-hydroxyethyl)piperazino]acetyl]-5H-pyrido[2,3-b][1,5]benzodiazepin-5-thione is heated to about 200° C. with ethyl carbazate to give 2,9-dihydro-9-[[4-(2-hydroxyethyl)-piperazino]acetyl]-3H-pyrido[3,2-c]-s-triazolo[4,3-a][1,5]benzodiazepin-3-one.

EXAMPLE 19

6,7-Dibromo-2,9-dihydro-9-[[4-(2-hydroxyethyl)-piperazino]acetyl]-3H-pyrido[3,2-c]-s-triazolo[4,3-a][1,5]-benzodiazepin-3-one In the manner given in Example 13, 8,9-dibromo-6,11-dihydro-11-[[4-(2-hydroxyethyl)-piperazino]acetyl]-5H-pyrido[2,3-b][1,5]benzodiazepin-5-thione is heated to about 200° C. with ethyl carbazate to give 6,7-dibromo-2,9-dihydro-9-[[4-(2-hydroxyethyl)piperazino]acetyl]-3H-pyrido[3,2-c]-s-triazolo[4,3-a][1,5]benzodiazepin-3-one.

EXAMPLE 20

2,9-Dihydro-9-(pyrrolidinoacetyl)-3H-pyrido-[3,2-c]-s-triazolo[4,3-a][1,5]benzodiazepin-3-one In the manner given in Example 13, 6,11-dihydro-11-(pyrrolidinoacetyl)-5H-pyrido[2,3-b][1,5]benzodiazepin-5-thione is heated to about 200° C. with ethyl carbazate to give 2,9-dihydro-9-(pyrrolidinoacetyl)-3H-pyrido[3,2-c]-s-triazolo[4,3-a][1,5]benzodiazepin-3-one.

EXAMPLE 21

2,9-Dihydro-9-(piperidinoacetyl)-3H-pyrido-[3,2-c]-s-triazolo[4,3-a][1,5]benzodiazepin-3-one In the manner given in Example 13, 6,11-dihydro-11-(piperidinoacetyl)-5H-pyrido[2,3-b][1,5]benzodiazepin-5-thione is heated to about 200° C. with ethyl carbazate to give 2,9-dihydro-9-(piperidinoacetyl)-3H-pyrido[3,2-c]-s-triazolo[4,3-a][1,5]benzodiazepin-3-one.

EXAMPLE 22

2,9-Dihydro-9-[(4-methylpiperazino)acetyl]-3H-pyrido[3,2-c]-s-triazolo[4,3-a][1,5]benzodiazepin-3-one In the manner given in Example 13, 6,11-dihydro-11-[(4-methylpiperazino)acetyl]-5H-pyrido[2,3-b][1,5]benzodiazepin-5-thione is heated to about 200° C. with ethyl carbazate to give 2,9-dihydro-11-[(4-methylpiperazino)acetyl]-3H-pyrido-[3,2-c]-s-triazolo[4,3-a][1,5]benzodiazepin-3-one.

EXAMPLE 23

6,7-Dimethyl-2,9-dihydro-9-[[4-(2-hydroxyethyl)-piperazino]acetyl]-3H-pyrido[3,2-c]-s-triazolo-[4,3-a][1,5]benzodiazepin-3-one In the manner given in Example 11, 8,9-dimethyl-6,11-dihydro-11-[[4-(2-hydroxyethyl)-piperazino]acetyl]-5H-pyrido[2,3-b][1,5]benzodiazepin-5-thione is heated to about 200° C. with ethyl carbazate to give 6,7-dimethyl-2,9-dihydro-9-[[4-(2-hydroxyethyl)piperazino]acetyl]-3H-pyrido[3,2-c]-s-triazolo[4,3-a][1,5]benzodiazepin-3-one.

EXAMPLE 24

6,7-Dimethyl-2,9-dihydro-9-[(4-methylpiperazino)-acetyl]-3H-pyrido[3,2-c]-s-triazolo[4,3-a][1,5]benzodiazepin-3-one In the manner given in Example 11, 8,9-dimetbhyl-6,11-dihydro-11-[(4-methylpiperazino)acetyl]-5H-pyrido[2;3-b]-[1,5]benzodiazepin-5-thione is heated to about 200° C. with ethyl carbazate to give 6,7-dimethyl-2,9-dihydro-9-[(4-methylpiperazino)acetyl]-3H-pyrido[3,2-c]-s-triazolo-[4,3-a][1,5]benzodiazepin-3-one.

In the manner given in the preceding examples 11 through 20, other compounds of formula III can be synthesized. Representative compounds thus obtained include:

6- and 7-fluoro-2,9-dihydro-9-[(dipropylamino)acetyl]-3H-pyrido[3,2-c]-s-triazolo[4,3-a][1,5]benzodiazepin-3-one;
6,7-di(trifluoromethyl)-2,9-dihydro-9-[(dipropylamino)-acetyl]-3H-pyrido[3,2-c]-s-triazolo[4,3-a][1,5]benzodiazepin-3-one;
8-cloro-9-fluoro- and 9-chloro-8-fluoro-2,9-dihydro-9-[[4-(2-hydroxyethyl)piperazino]acetyl]-3H-pyrido[3,2-c]-s-triazolo[4,3-a][1,5]benzodiazepin-3-one;
2,9-dihydro-9-[(diethylamino)acetyl]-3H-pyrido[3,2-c]-s-triazolo[4,3-a][1,5]benzodiazepin-3-one;
6,7-dimethyl-2,9-dihydro-9-[(dimethylamino)acetyl]-3H-pyrido[3,2-c]-s-triazo[4,3-a][1,5]benzodiazepin-3-one;
6,7-difluoro-2,9-dihydro-9-[(dipropylamino)acetyl]-3H-pyrido[ 3,2-c]-s-triazolo[4,3-a][1,5]benzodiazepin-3-one;
6,7-diethyl-2,9-dihydro-9-(pyrrolidinoaceyl)-3H-pyrido-[3,2-c]-s-triazolo[4,3-a][1,5]benzodiazepin-3-one;
6,7-diisopropyl-2,9-dihydro-9-(piperidinoacetyl)-3H-pyrido[3,2-c]-s-triazolo[4,3-a][1,5]benzodiazepin-3-one; and the like.

EXAMPLE 25

2,9-Dihydro-2-methyl-9-[(dimethylamino)acetyl]-3H-pyrido[3,2-c]-s-triazolo[4,3-a][1,5]benzodiazepin-3-one Sodium hydride (0.178 g., 4.21 mmoles of a 57% dispersion in mineral oil) is added to a solution of 2,9-dihydro-9-[(dimethylamino)acetyl]-3H-pyrido[3,2-c]-s-triazolo[4,3-a][1,5]benzodiazepin-3-one (4.21 mmoles) in 50 ml. of dimethylformamide and the mixture is heated at 95° C. for 35 minutes. The mixture is cooled to 50° C., a solution of methyliodide (4.21 mmole) is added and heating is continued at 95° C. for 21 hours. The mixture is evaporated and methylene chloride-water is added to the residue. The organic layer is separated and extracted three times with 10 ml. portions of 10% aqueous hydrochloric acid. The acid extract is cooled, made alkaline with 15% aqueous sodium hydroxide and the basic mixture is extracted with methylene chloride. The extract is washed with saturated salt solution, dried over anhydrous magnesium sulfate and evaporated. Crystallization of the residue from ether gives 2,9-dihydro-2-methyl-9-[(dimethylamino)acetyl]-3 H-pyrido[3,2-c]-s-triazolo[4,3-a]-[1,5]benzodiazepine.

EXAMPLE 26

2,9-Dihydro-2-[2-(dimethylamino)ethyl]-9-[(dipropylamino)acetyl]-3H-pyrido[3,2-c]-s-triazolo[4,3-a]-[1,5]benzodiazepin-3-one In the manner given in Example 21, to 2,9-dihydro-9-[(dipropylamino)acetyl]-3H-pyrido[3,2-c]-s-triazolo[4,3-a]-[1,5]benzodiazepin-3-one in dimethylformamide is added a solution of sodium hydride in mineral oil. The mixture is allowed to react at about 95° C. for 40 minutes and after cooling with (2-chloroethyl)dimethylamine in xylene is added. The mixture is kept at 95°–100° C. for a period of 22 hours, evaporated and worked up as in example 25 to give 2,9-dihydro-2-[(dimethylamino)ethyl]-9-[(dipropylamino)acetyl]-3H-pyrido[3,2-c]-s-triazolo[4,3-a][1,5]-benzodiazepin-3-one.

EXAMPLE 27

6,7-Dimethyl-2,9-dihydro-2-[3-(dimethylamino)-propyl]-9-[(dipropylamino)acetyl]-3H-pyrido[3,2-c]-s-triazolo[4,3-a][1,5]benzodiazepin-3-one In the manner given in Example 25, to 6,7-dimethyl-9-[(dipropylamino)acetyl]-3H-pyrido[3,2-c]-s-triazolo[4,3-a]-[1,5]benzodiazepin-3-one in dimethylformamide is added a solution of sodium hydride in mineral oil. The mixture is allowed to react at about 95° C. for 40 minutes and after cooling 3-(dimethylamino)-propylchloride in xylene is added. The mixture is kept at 95°–100° C. for a period of 22 hours, evaporated and worked up as in example 21 to give 6,7-dimethyl-2,9-dihydro-2-[3-(dimethylamino)-propyl]-9-[(dipropylamino)acetyl]-3H-pyrido[3,2-c]-s-triazolo[4,3-a][1,5]benzodiazepine-3-one.

EXAMPLE 28

6,7-Dichloro-2,9-dihydro-2-[2-[4-(2-hydroxyethyl)-piperazino]ethyl]-9-[(dipropylamino)acetyl]-3H-pyrido[3,2-c]-s-triazolo[4,3-a][1,5]benzodiazepin-3-one In the manner given in Example 25, to 6,7-dichloro-2,9-dihydro-9-[(dipropylamino)acetyl]-3H-pyrido[3,2-c]-s-triazolo[4,3-a][1,5]benzodiazepin-3-one in dimethylformamide is added a solution of sodium hydride in mineral oil. The mixture is allowed to react at about 95° C. for 40 minutes and after cooling 1-(2-chloroethyl)-4-(2-hydroxymethyl)piperazine in xylene is added. The mixture is kept at 95°–100° C. for a period of 22 hours, evaporated and worked up as in example 25 to give 6,7-dichloro-2,9-dihydro-2-[2-[4-(2-hydroxyethyl)piperazino]-ethyl]-9-[(dipropylamino)acetyl]-3H-pyrido[3,2-c]-s-triazolo[4,3-a][1,5]benzodiazepine-3-one.

EXAMPLE 29

6,7-Dibromo-2,9-dihydro-2-propyl-9-[(diethylamino)acetyl]-3H-pyrido[3,2-c]-s-triazolo[4,3-a][1,5]-benzodiazepin-3-one In the manner given in Example 25, to 6,7-dibromo-9-[(diethylamino)acetyl]-3H-pyrido[3,2-c]-s-triazolo-[4,3-a][1,5]benzodiazepin-3-one in dimethylformamide is added a solution of sodium hydride in mineral oil. The mixture is allowed to react at about 95° C. for 40 minutes and after cooling propyl chloride in xylene is added. The mixture is kept at 95°–100° C. for a period of 22 hours, evaporated and worked up as in exanmple 25 to give 6,7-dibromo-2,9-dihydro-2-propyl-9-[(diethylamino)acetyl]-3H-pyrido[3,2-c]-s-triazolo[4,3-a][1,5]-benzodiazepin-3-one.

EXAMPLE 30

2,9-Dihydro-2-(2-piperidinoethyl)-3H-pyrido-9-[[4-(2-hydroxyethyl)piperazino]acetyl]-3H-pyrido-[3,2-c]-s-triazolo[4,3-a][1,5]benzodiazepin-3-one In the manner given in Example 25, to 2,9-dihydro-9[[4-(2-hydroxyethyl)piperazino]acethyl]-3H-pyrido[3,2-c]-s-triazolo[4,3-a][1,5]benzodiazepin-3-one in dimethylformamide is added a solution of sodium hydride in mineral oil. The mixture is allowed to react at about 95° C. for 40 minutes and after cooling (2-piperidinoethyl)chloride in xylene is added. The mixture is kept at 95°–100° C. for a period of 22 hours, evaporated and worked up as in example 25 to give 2,9-dihydro-2-(2-piperidinoethyl)-9-[[4-(2-hydroxyethyl)piperazino]acetyl]-3H-pyrido[3,2-c]-s-traizolo[4,3-a][1,5]benzodiazepin-3-one.

EXAMPLE 31

2,9-Dihydro-2-methyl-9-[[4-(2-hydroxyethyl)-piperazino]acetyl]-3H-pyrido[3,2-c]-s-triazolo[4,3-a]-[1,5]benzodiazepin-3-one In the manner given in Example 25, 2,9-dihydro-1 1-[[4-(2-hydroxyethyl)piperazino]acetyl]-3H-pyrido[3,2-c]-s-traizolo[4,3-a][1,5]benzodiazepin-3-one in dimethylformamide is added a solution of sodium hydride in mineral oil. The mixture is allowed to react at about 95° C. for 40 minutes and after cooling methyl chloride in xylene is added. The mixture is kept at 95°–100° C. for a period of 22 hours, evaporated and worked up as in example 25 to give 2,9-dihydro-2-methyl-9-[[4-(2-hydroxyethyl)-piperazino]acetyl]-3H-pyrido[3,2-c]-s-triazolo[4,3-a][1,5]benzodiazepin-3-one.

EXAMPLE 32

2,9-Dihydro-2-(2-pyrrolidinoethyl)-9-(pyrrolidinoacetyl)-3H-pyrido[3,2-c]-s-triazolo[4,3-a][1,5]benzodiazepin-3-one In the manner given in Example 25, to 2,9-dihydro-9-[(pyrrolidino)acetyl]-3H-pyrido[3,2-c]-s-triazolo[4,3-a]-[1,5]benzodiazepin-3-one in dimethylformamide is added a solution of sodium hydride in mineral oil. The mixture is allowed to react at about 95° C. for 40 minutes and after cooling (2-pyrrolidinoethyl)chloride in xylene is added. The mixture is kept at 95°–100° C. for a period of 22 hours, evaporated and worked up as in example 25 to give 2,9-dihydro-2-(2-pyrrolidinoethyl)-9-(pyrrolidinoacetyl)-3H-pyrido[3,2-c]-s-triazolo[4,3-a]-[1,5]benzodiazepin-3-one.

EXAMPLE 33

2,9-Dihydro-2-[2-(dimethylamino)ethyl]-9-(piperidinoacetyl)-3H-pyrido[3,2-c]-s-triazolo[4,3-a]-[1,5]benzodiazepin-3-one In the manner given in Example 25, to 2,9-dihydro-9-(piperidinoacetyl)-3H-pyrido[3,2-c]-s-triazolo-[4,3-a][1,5]benzodiazepin-3-one in dimethylformamide is added a solution of sodium hydride in mineral oil. The mixture is allowed to react at about 95° C. for 40 minutes and after cooling (2-chloroethyl)dimethylamine in xylene is added. The mixture is kept at 95°–100° C. for a period of 22 hours, evaporated and worked up as in example 25 to give 2,9-dihydro-2-[2-(dimethylamino)ethyl]-9-(piperidinoacetyl)-3H-pyrido[3,2-c]-s-triazolo[4,3-a]-[1,5]benzodiazepin-3-one.

EXAMPLE 34

2,9-Dihydro-2-(3-pyrrolidinopropyl)-9-[(4-methylpiperazino)acetyl]-3H-pyrido[3,2-c)-s-triazolo-[4,3-a][1,5]benzodiazepine-3-one In the manner given in Example 25, to 2,9-dihydro-9-[(4-methylpiperazino)acetyl]-3H-pyrido[3,2-c]-s-triazolo[4,3-a][1,5]benzodiazepin-3-one in dimethyl-formamide is added a solution of sodium hydride in mineral oil. The mixture is allowed to react at about 95° C. for 40 minutes and after cooling (3-pyrrolidino-propyl)chloride in xylene is added. The mixture is kept at 95°–100°C. for a period of 22 hours, evaporated and worked up as in example 25 to give 2,9-dihydro-2-(3-pyrrolidinopropyl)-9-[(4-methylpiperazino)acetyl]-3H-pyrido[3,2-c]-s-triazolo[4,3-a][1,5]benzodiazepin-3-one.

EXAMPLE 35

6,7-Difluoro-2,9-dihydro-2-[2-(4-methylpiperazino)ethyl]-9-[(dipropylamino)acetyl]-3H-pyrido-[3,2-c]-s-triazolo[4,3-a][1,5]benzodiazepin-3-one In the manner given in Example 25, to 6,7-difluoro-2,9-dihydro-9-[(dipropylamino)acetyl]-3H-pyrido[3,2-c]-s-triazolo[4,3-a][1,5]benzodiazepin-3-one in dimethylforamide is added a solution of sodium hydrided in mineral oil. The mixture is allowed to react at about 95°C. for 40 minutes and after cooling [2-(4-methylpiperazino)-ethyl]chloride in xylene is added. The mixture is kept at 95°–100° C. for a period of 22 hours, evaporated and worked up as in example 25 to give 6,7-difluoro-2.9-dihydro-2-[2-(4-methyl-piperazino)ethyl]-9-[(dipropylamino)acetyl]-3H-pyrido[3,2-c]-s-triazolo[4,3-a][1,5]-benzodiazepin-3-one.

EXAMPLE 36

6,7-Dimethyl-2,9-dihydro-2-[3-dimethylamino)-propyl]-9-[(dimethylamino)acetyl]-3H-pyrido[3,2-c]-s-triazolo[4,3-a][1,5]benzodiazepin-3-one In the manner given in Example 25, to 6,7-dimethyl-2,9-dihydro-9-[(dimethylamino)acetyl]-3H-pyrido[3,2-c]-s-triazolo[4,3-a][1,5]benzodiazepin-3-one in dimethylformamide is added a solution of sodium hydride in mineral oil. The mixture is allowed to react to about 95° C. for 40 minutes and after cooling [3-(dimethylamino)-propyl]chloride in xylene is added. The mixture is kept at 95°–100° C. for a period of 22 hours, evaporated and worked up as in example 25 to give 6,7-dimethyl-2,9-dihydro-2-[3-(dimethylamino)propyl]-9-[(dimethylamino)-acetyl]-3H-pyrido[3,2-c]-s-triazolo[4,3-a][1,5]benzodiazepin-3-one.

EXAMPLE 37

6,7-Diethyl-2,9-dihydro-2-(3-pyrrolidinopropyl)-9-(pyrrolidinoacetyl)-3H-pyrido[3,2-c]-s-triazolo[4,3-a][1,5]benzodiazepin-3-one In the manner given in Example 25, to 6,7-diethyl-2,9-dihydro-9-(pyrrolidinoacetyl)-3H-pyrido[3,2-c]-s-triazolo[4,3-a][1,5]benzodiazepin-3-one in dimethyl-formamide is added a solution of sodium hydride in mineral oil. The mixture is allowed to react at about 95° C. for 40 minutes and after cooling (3-pyrrolidinopropyl)chloride in xylene is added. The mixture is kept at 95°–100° C. for a period of 22 hours, evaporated and worked up as in example 25 to give 6,7-diethyl-2,9-dihydro-2-(3-pyrrolidinopropyl)-9-(pyrrolidinoacetyl)-3H-pyrido[3,2-c]-s-triazolo[4,3-a]]1,5]benzodiazepin-3-one.

EXAMPLE 38

6-Chloro-7-fluoro- and 6-fluoro-7-chloro-2,9-dihydro-2-ethyl-9-[[4-(2-hydroethyl)piperazino]acetyl]-3H-pyrido[3,2-c]-s-triazolo[4,3-a][1,5]benzodiazepin-3-one In the manner given in Example 21, to a mixture of 6-chloro-7-fluoro- and 6-fluoro-7-chloro-2,9-dihydro-9-[[4-(2-hydroxyethyl)piperazino]acetyl]-3H-pyrido[3,2-c]-s-triazolo[4,3-a][1,5]benzodiazepin-3-one in dimethylformamide is added a solution of sodium hydride in mineral oil. The mixture is allowed to react at about 95° C. for 40 minutes and after cooling ethyl iodide in xylene is added. The mixture is kept at 95°–100° C. for a period of 22 hours, evaporated and worked up as in example 25 to give a mixture of 6-chloro-7-fluoro- and 6-fluoro-7-chloro-2,9-dihydro-2-ethyl-9-[[4-(2-hydroxyethyl)piperazino]acetyl]-3H-pyrido[3,2-c]-s-triazolo[4,3-a][1,5]benzodiazepin-3-one.

EXAMPLE 39

6,7-Dimethyl-2,9-dihydro-2-[3-(dimethylamino)-propyl]-9-[[4-(2-hydroxyethyl)piperazino]acetyl]-3H-pyrido[3,2-c]-s-triazolo[4,3-a][1,5]benzodiazepin-3-one.

In the manner given in Example 25, to 6,7-dimethyl-9-[[4-(2-hydroxyethyl)piperazino]acetyl]-3H-pyrido[3,2-c]-s-triazolo[4,3-a][1,5]benzodiazepin-3-one in dimethylformamide is added a solution of sodium hydride in mineral oil. The mixture is allowed to react at about 95° C. for 40 minutes and after cooling [3-(dimethylamino)propyl]-chloride in xylene is added. The mixture is kept at 95°–100° C. for a period of 22 hours, evaporated and worked up as in example 25 to give 6,7-dimethyl-2,9-dihydro-2-[3-(dimethylamino)propyl]-9-[[4-(2-hydroxyethyl)-piperazino]acetyl]-3H-pyrido[3,2-c]-s-triazolo]4,3-a]-[1,5]benzodiazepin-3-one.

EXAMPLE 40

6,7-Dimethyl-2,9-dihydro-2-[3-(dimethylamino)-propyl]-9-[(4-methylpiperazino)acetyl]-3H-pyrido[3,2-c]-s-triazolo[4,3-a][1,5]benzodiazepin-3-one In the manner given in Example 21, to 6,7-dimethyl-2,9-dihydro-9-[(4-methylpiperazino)acetyl]-3H-pyrido[3,2-c]-s-triazolo[4,3-a][1,5]benzodiazepin-3-one in dimethylformamide is added a solution of sodium hydride in mineral oil. The mixture is allowed to react at about 95° C. for 40 minutes and after cooling [3-(dimethylamino)propyl]chloride in xylene is added. The mixture is kept at 95°–100° C. for a period of 22 hours, evaporated and worked up as in example 25 to give 6,7-dimethyl-2,9-dihydro-2-[3-(dimethylamino)propyl]-9-[(4-methylpiperazino)-acetyl]-3-H-pyrido[3,2-c]-s-triazolo[4,3-a][1,5]benzodiazepin-3-one.

In the manner given in the preceding examples, other compounds of formula IV can be synthesized. Representative compounds, thus obtained, include:

6- and 7-fluoro-2,9-dihydro-2-methyl-9-[(dipropylamino)-acetyl]-3H-pyrido[3,2-c]-s-triazolo[4,3-a][1,5]benzodiazepin-3-one;
6,7-di(trifluoromethyl)-2,9-dihydro-2-[3-(diethylamino)-propyl]-9-[(dipropylamino)acetyl]-3H-pyrido[3,2-c]-s-triazolo[4,3-a][1,5]benzodiazepin-3-one;
2,9-dihydro-2-[[4-(2-hydroxyethyl)piperazino]ethyl]-9-[(diethylamino)acetyl]-3H-pyrido[3,2-c]-s-triazolo[4,3-a]-[1,5]benzodiazepin-3-one;
6,7-dimethyl-2,9-dihydro-2-isopropyl-9-[(dimethylamino)-acetyl]-3H-pyrido[3,2-c]-s-triazolo[4,3-a][1,5]benzodiazepin-3-one;
6,7-difluoro-2,9-dihydro-2-[(4-methylpiperazino)ethyl]-9-[(dipropylamino)acetyl]-3H-pyrido[3,2-c]-s-triazolo[4,3-a]-[1,5]benzodiazepin-3-one;
6,7-diisopropyl-2,9-dihydro-2-[3-(4-methylpiperazino)-propyl]-9-(piperidinoacetyl)-3H-pyrido[3,2-c]-s-triazolo[4,3-a][1,5]benzodiazepin-3-one;
6,7-diethyl-2,9-dihydro-2-(2-pyrrolidinoethyl)-9-(pyrrolidinoacetyl)-3H-pyrido[3,2-c]-s-triazolo[4,3-a][1,5]benzodiazepin-3-one;
6,7-dimethyl-2,9-dihydro-2-propyl-9-[(4-methylpiperazino)-acetyl]-3H-pyrido[3,2-c]-s-triazolo[4,3-a]benzodiazepin-3-one;
6,7-dibromo-2,9-dihydro-2-isopropyl-9-[[4-(2-hydroxyethyl)piperazino]acetyl]-3H-pyrido[3,2-c]-s-triazolo[4,3-a][1,5]benzodiazepin-3-one;
6,7-dipropyl-2,9-dihydro-2-methyl-9-[(dimethylamino)-acetyl]-3H-pyrido[3,2-c]-s-triazolo[4,3-a][1,5]benzodiazepin-3one;

and the like.

The novel compounds of formula IV (including III, IVA, IVB, and IVC) can be reacted with selected acids e.g. hydrochloric, hydrobromic, sulfuric, phosphoric, tartaric, citric, lactic, cyclohexanesulfamic, toluenesulfonic and other acids to give the corresponding pharmaceutically acceptable acid addition salts. This reaction is carried out under conventional conditions, in solvents such as ether, dioxane, tetrahydrofuran, and the like at room temperatures, and the resulting precipitated salts are collected by filtration. These salts can be used in place of the free base for the same pharmaceutical purpose described before.

I claim:
1. A compound of the formula IV wherein R' and R'' are alkyl of 1 to 3 carbon atoms or $$-N\begin{matrix}R'\\R''\end{matrix}$$

is pyrrolidino, piperidino, 4-methylpiperazino, or [4-(2-hydroxyethyl)piperazino] wherein $R_2$ and $R_3$ are hydrogen, chloro, bromo, trifluoromethyl or alkyl defined as above; and wherein $R_4$ is hydrogen, alkyl as defined above or $$-(CH_2)_n-N\begin{matrix}R'\\R''\end{matrix}$$

in which $n$ is an integral number of 2 or 3 and R', R'' and $$-N\begin{matrix}R'\\R''\end{matrix}$$

are defined as above, or the pharmacologically acceptable acid addition salts thereof.

2. A compound according to claim 1 of the formula IVB:

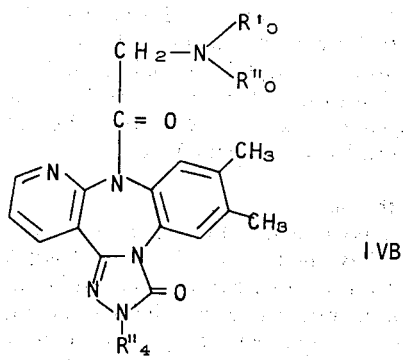

wherein R'₀, R''₀ are alkyl of 1 to 3 carbon atoms or together

is 4-methylpiperazino or [4-(2-hydroxyethyl)-piperazino] and R''₄ is methyl or

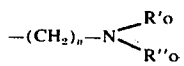

in which n is an integral number 2 or 3 and R'₀, R''₀ or

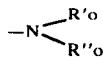

are defined as above or the pharmacologically acceptable acid addition salts thereof.

3. A compound according to claim 1 of the formula IVC:

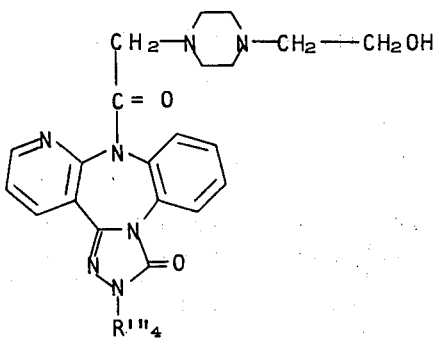

wherein R'''₄ is hydrogen or alkyl of 1 to 3 carbon atoms, inclusive, or the pharmacologically acceptabe acid addition salts thereof.

4. A compound according to claim 1, wherein R' and R'' are methyl, R₂, R₃, and R₄ are hydrogen, and the compound is therefore 2,9-dihydro-9-[(dimethylamino)acetyl]-3H-pyrido[3,2-c]-s-triazolo[4,3-a][1,5]benzodiazepin-3-one.

5. A compound according to claim 1, wherein R' and R'' are propyl, R₂, R₃, and R₄ are hydrogen and the compound is therefore 2,9-dihydro-9-[(dipropylamino)acetyl]-3H-pyrido[3,2-c]-s-triazolo[4,3-a][1,5]benzodiazepin-3-one.

6. A compound according to claim 1, wherein R' and R'' are propyl, R₂ and R₃ are chloro, R₄ is hydrogen, and the compound is therefore 6,7-dichloro-2,9-dihydro-9-[(dipropylamino)acetyl]-3H-pyrido[3,2-c]-s-triazolo-[4,3-a][1,5]benzodiazepin-3-one.

7. A compound according to claim 3, wherein R'''₄ is hydrogen, and the compound is therefore 2,9-dihydro-9-[[4-(2-hydroxyethyl)piperazino]acetyl[-3H-pyrido[3,2-c]-s-triazolo[4,3-a][1,5]benzodiazepin-3-one.

8. A compound according to claim 1, wherein the group

taken together is 4-methylpiperazino, R₂, R₃, and R₄ are hydrogen and the compound is therefore 2,9-dihydro-9-[(4-methylpiperazino)acetyl]-3H-pyrido[3,2-c]-s-triazolo-[4,3-a][1,5]benzodiazepin-3one.

9. A compound according to claim 2, wherein R'₀ and R''₀ are propyl, R''₄ is 3-(dimethylamino)propyl and the compound is therefore 6,7-dimethyl-2,9-dihydro-2-[3-(dimethylamino)propyl]-9-[(dipropylamino)acetyl]-3H-pyrido-[3,2-c]-s-triazolo[4,3-a][1,5]benzodiazepin-3-one.

10. A compound according to claim 2, wherein the group

taken together is 4-[(2-hydroxyethyl)piperazino], R''₄ is 3-(dimethylamino)propyl and the compound is therefore 6,7-dimethyl-2,9-dihydro-2-[3-(dimethylamino)-propyl]-9-[[4-(2-hydroxyethyl)-piperazino]acetyl]-3H-pyrido[3,2-c]-s-triazolo[4,3-a][1,5]benzodiazepin-3-one.

* * * * *